United States Patent [19]

Clark

[11] 4,447,617
[45] May 8, 1984

[54] PROCESS FOR THE PREPARATION OF 2-AMINO-6-NITROBENZOTHIAZOLE

[75] Inventor: R. Donald Clark, Kingsport, Tenn.

[73] Assignee: Eastman Kodak Company, Rochester, N.Y.

[21] Appl. No.: 368,240

[22] Filed: Apr. 14, 1982

[51] Int. Cl.$^3$ .................................... C07D 277/82
[52] U.S. Cl. .................................... 548/164; 548/158
[58] Field of Search ............................. 548/164, 158

[56] References Cited

U.S. PATENT DOCUMENTS 3,781,297  2/1983  Pawellek ...................... 548/164

OTHER PUBLICATIONS

Metzger, Thiazoles and its Derivatives, Part 2, pp. 392–393, (1979).

Primary Examiner—Robert Gerstl
Attorney, Agent, or Firm—Gary C. Bailey; Daniel B. Reece, III

[57] ABSTRACT

Disclosed is a novel process for the preparation of 2-amino-6-nitrobenzothiazole which comprises contacting 2-mercapto-6-nitrobenzothiazole with hydrogen peroxide in the presence of ammonia. The reaction is conveniently conducted in an aqueous medium. The mole ratio of hydrogen peroxide to mercaptan is preferably about 4:1 and the reaction is conducted at a temperature of about 50° to 100° C.

9 Claims, No Drawings

PROCESS FOR THE PREPARATION OF 2-AMINO-6-NITROBENZOTHIAZOLE

BACKGROUND OF THE INVENTION

This invention relates to the preparation of 2-amino-6-nitrobenzothiazole which is useful in azo dye synthesis.

Various processes for the preparation of 2-amino-6-nitrobenzothiazole are known. For example Pubbl. ist. chim. univ. Bologna No. 2, 3–10 (1943); Chemical Abstracts 41:754 discloses the chlorination of 2-mercaptobenzothiazole to give 2-chlorobenzothiazole which is then treated with nitric and sulfuric acids to give 2-chloro-6-nitrobenzothiazole. The 2-chloro-6-nitrobenzothiazole is then treated with alcoholic ammonia under pressure at 140° to give 2-amino-6-nitrobenzothiazole. No yields are stated in the English abstract.

It has also been reported [see J. Amer. Chem. Soc. 49, 1748 (1927)] that treatment of 2-mercapto-6-nitrobenzothiazole with concentrated aqueous ammonia under pressure at 160° C. followed by crystallization from alcohol and treatment with bone black gives 2-amino-6-nitrobenzothiazole in small yield.

According to the process of this invention, 2-amino-6-nitrobenzothiazole is obtained in good yield and without the use of extreme reaction conditions which the prior art processes require. The compound is obtained according to the process of my invention by contacting 2-mercapto-6-nitrobenzothiazole in the presence of ammonia with hydrogen peroxide. While hydrogen peroxide has previously been used in the preparation of hydroxybenzothiazole from mercaptobenzothiazole (see J. Pharm. Soc. Japan 58, 29–37 (1938); Chemical Abstracts 32:3759), its usefulness in the preparation of 2-amino-6-nitrobenzothiazole from 2-mercapto-6-nitrobenzothiazole has heretofore been undisclosed.

SUMMARY OF THE INVENTION

The process of the present invention relates to the preparation of 2-amino-6-nitrobenzothiazole by a process comprising contacting 2-mercapto-6-nitrobenzothiazole with hydrogen peroxide in the presence of ammonia.

DETAILED DESCRIPTION OF THE INVENTION

The present invention concerns the preparation of 2-amino-6-nitrobenzothiazole. One embodiment of the process of my invention comprises contacting 2-mercapto-6-nitrobenzothiazole with hydrogen peroxide in the presence of ammonia to obtain 2-amino-6-nitrobenzothiazole. Since it is not necessary to isolate the 2-mercapto precursor, a second embodiment comprises the steps of treating 2,2'-dithiobis-6-nitrobenzothiazole with an alkali metal sulfite compound and then converting the resulting 2-mercapto derivative to 2-amino-6-nitrobenzothiazole by the means described above. By the process of the second embodiment ammonia may optionally be added in the first step of treating 2,2'-dithiobis-6-nitrobenzothiazole with the alkali metal sulfite compound. The starting material, 2,2'-dithiobis-6-nitrobenzothiazole, is known in the art and is readily obtained by nitrating 2-mercaptobenzothiazole using fuming nitric acid and concentrated sulfuric acid according to known procedures.

The first embodiment of the invention comprises contacting 2-mercapto-6-nitrobenzothiazole with hydrogen peroxide in the presence of ammonia. The reaction is exothermic and therefore the hydrogen peroxide should be added gradually in order to maintain the reaction temperature within the desired range. The temperature can be varied, for example, from about 50° to 100° C., although temperatures in the range of about 55°–60° C. are preferred. The amount of hydrogen peroxide employed will ordinarily be at least one mole per mole of mercaptan and preferably the mole ratio is about 4:1. Of course greater amounts of hydrogen peroxide may be used but are not expected to afford any additional advantage.

Generally the ammonia is employed in an aqueous solution in concentrations of about 5% to 70% with 5–15% being preferred. The mole ratio of ammonia to mercaptan normally should be about 5–20:1. The weight ratio of water employed generally will be about 7 parts of water per 1 part of mercaptan. As will be recognized by those skilled in the art, these ratios can be varied widely but generally will confer no particular advantage. Upon completing the addition of the hydrogen peroxide, the reaction mixture is cooled and the product isolated by conventional means.

The second embodiment of my invention comprises treating 2,2'-dithiobis-6-nitrobenzothiazole with an alkali metal sulfite compound to obtain 2-mercapto-6-nitrobenzothiazole which then may be converted to 2-amino-6-nitrobenzothiazole as described hereinabove. The reduction of the disulfide bond using an alkali metal sulfite compound is not in itself unique. As indicated previously, if desired the ammonia may be present in the first step during the treatment of the 2,2'-dithiobis-6-nitrobenzothiazole. The mole ratio of ammonia to disulfide and the weight ratio of water to disulfide will be essentially equal to the ratios described in the first embodiment.

According to the process of the second embodiment the product of the first step, 2-mercapto-6-nitrobenzothiazole, is not isolated but is allowed to remain in the resulting reaction mixture for reaction with the hydrogen peroxide. The advantages of a continuous operation such as this are readily apparent.

The alkali metal sulfite compounds suitable for the present process are those of the sodium and potassium metals such as sodium sulfite, sodium bisulfite, sodium metabisulfite and potassium sulfite. Normally the amount employed will be at least one mole of sulfite compound for each mole of disulfide compound. To ensure complete reduction of the disulfide compound it is desirable to employ a slight excess of sulfite, up to about one mole excess, so that the mole ratio of sulfite to disulfide is about 2:1. The reaction temperature can vary from about 50° C. to about 100° C. with about 60° to 65° C. being preferred. While the reaction will ordinarily proceed at temperatures below about 50° C. the yield of mercaptan normally will be less.

By the process of this invention, 2-amino-6-nitrobenzothiazole is obtained in yields of about 85%. Moreover, the process may be carried out as a continuous operation without isolation of the intermediate mercaptan which serves to reduce the cost of the operation as well as the amount of operating time. Of course with an available supply of 2-mercapto-6-nitrobenzothiazole the process conveniently is carried out in one step. The product compound is widely known in the art as a useful intermediate in the preparation of azo dyes.

The following examples are given to further illustrate the invention, but it is to be understood that the invention is not to be limited in any way by the details described therein.

EXAMPLE 1

A mixture of 167 g (1.0 mole) of 2-mercaptobenzothiazole and 600 ml. of 98% sulfuric acid is stirred and heated. Gas evolution begins at about 55°. Heating is continued to 75° over about 15 min. and then the temperature is controlled at 75° for 30 minutes. The solution is cooled to 10° and maintained while 70 g. (1.1 mole) of 98% nitric acid is added over a period of 30 min. The mixture is stirred at 10° for 30 minutes and then is gradually added to 1000 ml of water at 75°–85° over a period of 2-¼ hours. The solid is filtered off (60°–70°) and washed on the filter with three 500-ml portions of water. The solid is held wet for the next step. Total yield of 2,2'-dithiobis-6-nitrobenzothiazole calculated on a dry basis is 211 g.

EXAMPLE 2

The solid from the first step (~211 g) is mixed with 600 ml of water, 600 ml of 28% aqueous ammonia, and 130 g (1.03 mole) of sodium sulfite. The mixture is heated at 60°–65° until the disulfide is completely reduced (30–60 min.).

Hydrogen peroxide (454 g of a 30% solution) is gradually added over a period of 3–4 hours while maintaining the temperature at 55°–60°. The reaction is exothermic. When addition is complete, the mixture is cooled to 45°–50° and filtered. The solid is washed on the filter with three 500-ml portions of water and dried. The yield of 2-amino-6-nitrobenzothiazole is 166 g (85%).

The invention has been described in detail with particular reference to certain preferred embodiments thereof, but it will be understood that variations and modifications can be effected within the spirit and scope of the invention.

I claim:

1. Process for the preparation of 2-amino-6-nitrobenzothiazole which comprises contacting a mixture of 2-mercapto-6-nitrobenzothiazole and ammonia with hydrogen peroxide.

2. Process according to claim 1 wherein the contacting is carried out at a temperature of about 50° to about 100° C.

3. Process according to claim 1 wherein the mole ratio of hydrogen peroxide to mercaptan is about 1–4:1.

4. Process according to claim 1 wherein the ammonia is present in aqueous solution in about 5% to 70% concentration, the mole ratio of ammonia to mercaptan being about 5–20:1.

5. Process for the preparation of 2-amino-6-nitrobenzothiazole which comprises the steps of:
   A. Treating 2,2'-dithiobis-6-nitrobenzothiazole with an alkali metal sulfite compound in the presence of ammonia to obtain a reaction mixture containing 2-mercapto-6-nitrobenzothiazole;
   B. Contacting the reaction mixture of A with hydrogen peroxide.

6. Process according to claim 5 wherein the ammonia is present in an aqueous solution in about 5% to 70% concentration, the mole ratio of ammonia to disulfide compound being about 5–20:1.

7. Process according to claim 5 wherein the sulfite employed in step A is sodium sulfite, sodium bisulfite, sodium metabisulfite or potassium sulfite.

8. Process according to claim 7 wherein the mole ratio of sulfite compound to disulfide is about 1–2:1 and the mole ratio of hydrogen peroxide to mercaptan is about 1–4:1.

9. Process for the preparation of 2-amino-6-nitrobenzothiazole which comprises the steps of:
   A. Treating 2,2'-dithiobis-6-nitrobenzothiazole with sodium sulfite in the presence of ammonia, at a temperature of about 60° to 65° C. to obtain a reaction mixture containing 2-mercapto-6-nitrobenzothiazole, wherein the mole ratio of sulfite to disulfide is about 1–2:1 and the ammonia is present in aqueous solution in about 5% to 15% concentration, the mole ratio of ammonia to disulfide being about 5–20:1;
   B. Contacting the reaction mixture of (A) with hydrogen peroxide at about 55° to 60° C., wherein the mole ratio of hydrogen peroxide to mercaptan is about 1–4:1.

* * * * *